United States Patent [19]

Greene

[11] 4,301,319

[45] Nov. 17, 1981

[54] MANUFACTURE OF ALLENE FROM ACETONE

[75] Inventor: Janice L. Greene, Chagrin Falls, Ohio

[73] Assignee: Standard Oil Company, Cleveland, Ohio

[21] Appl. No.: 150,506

[22] Filed: May 16, 1980

[51] Int. Cl.³ ............................................. C07C 1/253
[52] U.S. Cl. ..................................................... 585/638
[58] Field of Search ................................ 585/638, 640

[56] References Cited

U.S. PATENT DOCUMENTS

| | | | |
|---|---|---|---|
| 2,419,142 | 4/1947 | Ipatieff et al. | 585/638 |
| 2,443,732 | 6/1948 | Ipatieff et al. | 585/638 |
| 4,039,584 | 8/1977 | Falbe et al. | 585/638 |

Primary Examiner—Curtis R. Davis
Attorney, Agent, or Firm—Gary R. Plotecher; Herbert D. Knudsen; Larry W. Evans

[57] ABSTRACT

Acetone is converted to allene by contacting the acetone with an alumina catalyst, such as γ-alumina, at a temperature between about 300° and 700° C.

5 Claims, No Drawings

MANUFACTURE OF ALLENE FROM ACETONE

BACKGROUND OF THE INVENTION

1. Field of the Invention

This invention relates to the preparation of allene from acetone in the presence of an alumina catalyst.

2. Description of the Prior Art

Various methods are known for preparing allene, typically in combination with methyl acetylene. The latter is an isomer of allene and the manufacture of one generally results in the manufacture of the other since the two are in a constant state of equilibrium. U.S. Pat. No. 2,510,550 teaches the manufacture of methyl acetylene from the alcoholysis of magnesium carbide. U.S. Pat. No. 2,649,485 teaches the manufacture of methyl acetylene and allene by subjecting a dihalogenated propane or mono-halogenated propylene to decomposition at a temperature between about 850°–1050° C. U.S. Pat. No. 2,755,319 teaches the manufacture of methyl acetylene by the dechlorination of 1,2-dichloropropane in the presence of sodium hydroxide. U.S. Pat. No. 2,818,456 teaches the preparation of allene by the decomposition of diketene at a temperature between about 510°–590° C. The decomposition is performed in a copper-lined reactor. Still other methods are known. See for example U.S. Pat. Nos. 2,848,520 and 2,925,451.

Various acid and bases have long been known to catalyze a variety of acetone condensation reactions. For example, U.S. Pat. No. 3,497,558 teaches that acetone and 45% aqueous potassium hydroxide heated to a temperature of about 220° C. under antogenous pressure yields mesityl oxide, isophorone and higher molecular weight products. U.S. Pat. No. 3,816,546 teaches the vapor phase condensation of acetone over magnesium oxide to produce 3,5-xylenol.

SUMMARY OF THE INVENTION

According to this invention, allene is prepared by contacting acetone with an alumina catalyst at a temperature between about 300° and 700° C.

DETAILED DESCRIPTION OF THE INVENTION

The general reaction of this invention is illustrated by equation I.

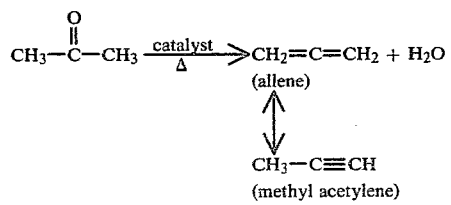

Acetone is reduced to allene and water and the allene can and usually does isomerize to form an equilibrium mixture of allene and methyl acetylene. The acetone can be used either alone or diluted with an essentially inert gas, such as nitrogen, argon, methanol, ethanol, benzene and the like. By "inert" is meant that the material is essentially non-reactive with acetone, allene, methyl acetylene, water or the catalyst at process conditions. Alternatively, the acetone can be supplied to the reaction in the form of a material that will convert to acetone (with or without the formation of a by-product) in the presence of the catalyst at reaction conditions. Exemplary of such materials are methyl ethyl ketone and acetonecyanohydrin.

Any alumina (aluminum oxide, $Al_2O_3$) material that can catalyze the reduction of acetone to allene and/or methyl acetylene can be used in the practice of this invention. The alumina can be used alone, diluted with another material, or promoted with a metal or some combination of metals. If diluted, the diluent can be essentially any support material such as silica, titania, zirconia, etc. Exemplary promoters include metals or their oxides from Groups IA, IIA, VIB, VIIB, VIII and lanthanides (rare-earth elements) of the Periodic Table (Condensed Chemical Dictionary, 9 Ed., p. 662, 1977), with the metals/metal oxides from Groups VIB and VIII being preferred. Platinum, chromium and their oxides are of particular interest as promoters. The metals can be present alone or in combination with one another and at least some portion of the metal is typically present in its oxide form. The alumina catalyst can be amorphous or highly crystalline in structure, such as a molecular sieve, and can be shaped or unshaped. Representative catalysts include Engelhard RD-150 (0.3% platinum on η-alumina), Harshaw Al-1706 (97% γ-alumina), Harshaw Cr-1403 (19% chromium oxide on alumina) and Linde SK-500 (a rare-earth exchanged aluminosilicate molecular sieve). If a promoter is employed, then it is generally employed in the amount of between about 0.1 and 10 weight percent based on the combined weight of the alumina and promoter.

The temperature at which this invention is practiced is typically between about 300° and 700° C. and preferably between about 350° and 550° C. Pressure is important to this invention only as it relates to temperature and can range from subatmospheric to superatmospheric. A typical pressure range is from about 0.1 to 200 atmospheres with a preferred pressure range of from about 0.5 to 2 atmospheres. Reaction time can also vary widely, from about a fraction of a second to excess of 10 hours but is typically and preferably within the range of about 15 to 120 seconds. The ratio of acetone to catalyst is not critical and is governed by convenience and economics. Although the invention can be practiced in either a batch or continuous mode, the latter is preferred.

Allene and methyl acetylene are useful intermmediates in many organic synthesis, particularly pharmaceutical manufacture.

The following examples are illustrative of certain specific embodiments of this invention. Unless indicated to the contrary, all parts and percentages are by weight.

SPECIFIC EMBODIMENTS

Procedure:

A stainless steel microreactor was charged with about 26 cc of catalyst crushed to about 14–42 standard mesh. The reactor was then heated and a feed stream comprising acetone was fed to the top of the reactor at a rate of approximately 93.3 ml per hour along with 94 cc/min. nitrogen as a sweep gas. The reactor effluent was then passed through a series of cold traps to remove condensible product and the off-gas was analyzed by gas chromotagraphy. The results of a number of different experiments are reported in the table.

TABLE

CONVERSION OF ACETONE TO ALLENE

| Example | Feed[1] | Catalyst[2] | Temp (°C.) | % Conversion to[3] Allene | Methyl Acetylene |
|---|---|---|---|---|---|
| 1 | Acetone | Harshaw Al-1706 | 550 | 26 | — |
| 2 | Acetone + methanol | " | " | 9 | 2 |
| 3 | Acetone + ethanol | " | " | 10.1 | — |
| 4 | Acetone + benzene | " | " | 0.9 | — |
| 5 | Acetone + benzene | | 500 | 7.5 | — |
| 6 | Acetone + methanol + $H_2O$ | " | 350 | 0.5 | — |
| 7 | Acetone + methanol + $H_2O$ | " | 400 | 2 | — |
| 8 | Acetone + methanol + $H_2O$ | " | 450 | 4 | — |
| 9 | Acetone + methanol + $H_2O$ | " | 500 | 10 | 1 |
| 10 | Acetone + methanol + $H_2O$ | " | 550 | 8.3 | — |
| 11 | Acetone + methanol | Harshaw Cr-1403 | 550 | 1 | — |
| 12 | Acetone + methanol + $H_2O$ | " | 550 | 50 | — |
| 13 | Methylethylketone | Harshaw Al-1796 | 550 | 7.4 | — |
| 14 | Acetonecyanhydrin + methanol + $H_2O$ | Engelhard Rd-150 | 400 | 1.5 | — |
| 15 | Same as 14 | " | 550 | 40 | 3 |
| 16 | Acetone + Benzene | Linde Sk-500 | 550 | 4.7 | — |

Acetone:methanol volume ratio = 1:5
Acetone:ethanol volume ratio = 1:5
Acetone:benzene volume ratio = 1:2.5
Acetone:methanol:$H_2O$ volume ratio = 1:5:1
Acetonecyanhydrin:methanol:$H_2O$ volume ratio = 1:5:1
Harshaw Al-1706 = 97%-$Al_2O_3$
Harshaw Cr-1403 = 19% $Cr_2O_3$ on $Al_2O_3$
Engelhard RD-150 = 0.3% Pt on —$Al_2O_3$
Linde Sk-500 = Rare-earth exchanged molecular seive.

Conversion to Allene = $\frac{\text{allene recovered} \times 100}{\text{acetone reacted}}$ Conversion to Methyl Acetylene = $\frac{\text{methylacetylene recovered} \times 100}{\text{acetone reacted}}$ The tabulated results demonstrate the operability of this invention. Acetone was reduced to allene, in some cases in combination with methyl acetylene, over several different alumina catalysts, both promoted and unpromoted, in the presence and absence of various diluent gases, and at several different temperatures. In example 13 the acetone was provided by the decomposition of methyl ethyl ketone.

Although this invention has been described in considerable detail by the preceding examples, this detail is for the purpose of illustration only and is not to be construed as a limitation upon the invention as described in the specification or in the depended claims.

The claimed invention is:

1. A method of preparing allene from acetone, the method comprising contacting acetone with an alumina catalyst at a temperature between about 300° and 700° C.

2. The method of claim 1 where the catalyst is promoted with at least one Group IA, IIA, VIB, VIIB or VIII metal or metal oxides.

3. The method of claim 1 where the catalyst is promoted with a Group VIB or VIII metal or metal oxide.

4. The method of claim 3 where the catalyst is promoted with platinum or chromium metal or metal oxide.

5. The method of claim 1 where the catalyst is selected from the group consisting of γ-alumina, platinum promoted η-alumina, chromium oxide promoted alumina and a rare-earth exchanged aluminosilicate molecular seive.

* * * * *